United States Patent [19]

Choi et al.

[11] Patent Number: 5,241,041

[45] Date of Patent: Aug. 31, 1993

[54] PHOTOCROSSLINKABLE POLYIMIDE AMMONIUM SALTS

[75] Inventors: Jin-O Choi, Amherst; John A. Tyrell, Williamsville, both of N.Y.

[73] Assignee: Occidental Chemical Corporation, Niagara Falls, N.Y.

[21] Appl. No.: 807,348

[22] Filed: Dec. 16, 1991

[51] Int. Cl.$^5$ .......................... C08G 69/26; C08G 73/10
[52] U.S. Cl. .......................... 528/353; 528/26; 528/35; 528/38; 528/41; 528/43; 528/125; 528/126; 528/170; 528/172; 528/173; 528/174; 528/179; 528/183; 528/185; 528/188; 528/220; 528/229; 528/350; 528/351
[58] Field of Search .......... 528/353, 26, 38, 41, 528/35, 43, 125, 126, 170, 172, 173, 174, 179, 183, 185, 188, 220, 229, 350, 351, 353

[56] References Cited

U.S. PATENT DOCUMENTS

| | | | |
|---|---|---|---|
| 4,243,743 | 1/1981 | Hiramoto et al. | 430/282 |
| 4,321,319 | 3/1982 | Shoji et al. | 528/327 |
| 4,480,009 | 10/1984 | Berger | 528/26 |
| 4,499,149 | 2/1985 | Berger | 528/26 |
| 4,520,075 | 5/1985 | Igarashi | 528/128 |
| 4,634,760 | 1/1987 | Takekoshi | 528/26 |
| 4,656,238 | 4/1987 | Kunimune | 528/26 |
| 4,672,099 | 6/1987 | Kunimune | 528/26 |
| 4,748,228 | 5/1988 | Shoji | 528/26 |
| 4,794,153 | 12/1988 | Rich | 528/26 |
| 4,826,916 | 5/1989 | Policastro | 528/26 |
| 4,829,131 | 5/1989 | Lee | 528/26 |
| 4,959,437 | 9/1990 | Kunimune | 528/26 |
| 4,970,283 | 11/1990 | Kunimune | 528/26 |
| 4,996,278 | 2/1991 | Lee | 528/26 |
| 4,997,908 | 3/1991 | Lee | 528/26 |
| 5,041,513 | 8/1991 | Okinoshima | 528/26 |
| 5,053,314 | 10/1991 | Yamaoka | 528/26 |
| 5,061,774 | 10/1991 | Park | 528/26 |
| 5,104,946 | 4/1992 | Lee | 528/26 |
| 5,104,958 | 4/1992 | Bolon | 528/26 |

*Primary Examiner*—John Kight, III
*Assistant Examiner*—P. Hampton-Hightower
*Attorney, Agent, or Firm*—Wayne A. Jones; Richard D. Fuerle

[57] ABSTRACT

Disclosed is a polyimide ammonium salt comprising the reaction product of an ethylenically unsaturated amine with an aromatic polyimide having pendant carboxylic acid groups, said polyimide comprising the reaction product of diamine and aromatic dianhydride, where the diamine comprises an aromatic carboxylic acid diamine having at least one carboxylic acid. A substrate can be coated with the polyimide ammonium salt by forming a composition of a crosslinking agent and a solution of the polyimide salt in an organic solvent, spreading the composition on the substrate, evaporating the solvent to form a coating, exposing at least some of the coating to actinic radiation to crosslink and insolubilize the exposed portions of the coating, and washing the unexposed portions away by dissolving them in an organic solvent.

22 Claims, No Drawings

PHOTOCROSSLINKABLE POLYIMIDE AMMONIUM SALTS

BACKGROUND OF INVENTION

This invention relates to polyimide ammonium salts that are photocrosslinkable. In particular, it relates to novel polyimides having pendant ammonium carboxylate groups that contain ethylenic unsaturation, and to their preparation and use.

Polyimides are used in the semiconductor industry as dielectric coatings on silicon chips. In the conventional process for making the coatings, a substrate is coated with a solution of a photocrosslinkable polyamic acid. The solvent is evaporated and the polyamic acid is crosslinked with actinic light to insolubilize it. The uncrosslinked portions are washed away with solvent and the remaining polyamic acid is heated to imidize it.

In a second method for forming a polyimide coating on a silicon chip, a solution of a soluble photocrosslinkable polyimide in an organic solvent is prepared and spread on the substrate. The solvent is evaporated and the polyimide is crosslinked and insolubilized with actinic light. Portions that were not exposed to the light are then washed away with the solvent. In both methods, a diamine containing an ethylenically unsaturation group is used as a monomer in preparing the polyimide to make it photocrosslinkable.

SUMMARY OF INVENTION

While the two hereinabove-described prior methods prepare polyimide coatings, in the method of this invention the coating is a polyimide ammonium salt. Instead of using diamines that contain ethylenic unsaturation, in this invention diamines are used that contain at least one carboxylic acid group. Not only are carboxylic acid diamines more readily available and easier to prepare than diamines containing ethylenic unsaturation, but they cannot crosslink during imidization as can diamines containing ethylenic unsaturation. After the polyimide is prepared, the pendant carboxylic acid groups on the polyimide are reacted with amines that contain ethylenic unsaturation, forming an ammonium carboxylate linkage. The ethylenic unsaturation in the amine crosslinks and insolubilizes the polyimide when it is exposed to actinic radiation.

DESCRIPTION OF INVENTION

The polyimides of this invention are prepared by the stoichiometric reaction in solution of aromatic dianhydride with diamine. Examples of suitable aromatic dianhydrides that can be used include:

1,2,5,6-naphthalene tetracarboxylic dianhydride;
1,4,5,8-naphthalene tetracarboxylic dianhydride;
2,3,6,7-naphthalene tetracarboxylic dianhydride;
2-(3',4'-dicarboxyphenyl) 5,6-dicarboxybenzimidazole dianhydride;
2-(3',4'-dicarboxyphenyl) 5,6-dicarboxybenzoxazole dianhydride;
2-(3',4'-dicarboxyphenyl 5,6-dicarboxybenzothiazole dianhydride;
2,2',3,3'-benzophenone tetracarboxylic dianhydride;
2,3,3',4'-benzophenone tetracarboxylic dianhydride;
3,3',4,4'-benzophenone tetracarboxylic dianhydride (BTDA);
2,2',3,3'-biphenyl tetracarboxylic dianhydride;
2,3,3',4'-biphenyl tetracarboxylic dianhydride;
3,3',4,4'-biphenyl tetracarboxylic dianhydride (BPDA);
bicyclo-[2,2,2]-octen-(7)-2,3,5,6-tetracarboxylic-2,3:5,6-dianhydride;
bis (3,4-dicarboxyphenyl) sulfone dianhydride;
bis (3,4-dicarboxyphenyl) sulfoxide dianhydride;
bis (3',4'-dicarboxyphenyl oxadiazole-1,3,4) paraphenylene dianhydride;
bis (3,4'-dicarboxyphenyl) 2,5-oxadiazole 1,3,4-dianhydride;
bis 2,5-(3',4'-dicarboxydiphenylether) 1,3,4-oxadiazole dianhydride;
bis (3,4-dicarboxyphenyl) ether dianhydride or oxydiphthalic anhydride (ODPA);
bis (3,4-dicarboxyphenyl) thioether dianhydride;
bisphenol A bisether dianhydride;
bisphenol S bisether dianhydride;
2,2'-bis (3,4-dicarboxyphenyl) hexafluoropropane dianhydride (6FDA);
hydroquinone bisether dianhydride;
bis (3,4-dicarboxyphenyl) methane dianhydride;
cyclopentadienyl tetracarboxylic acid dianhydride;
cyclopentane tetracarboxylic dianhydride;
ethylene tetracarboxylic acid dianhydride;
perylene 3,4,9,10-tetracarboxylic dianhydride;
pyromellitic dianhydride (PMDA);
tetrahydrofuran tetracarboxylic dianhydride; and
5,5-[2,2,2-trifluoro-1-(trifluoromethyl)ethylidene]bis-1,3-isobenzofurandione)

Preferred dianhydrides are BTDA, BPDA, PMDA, ODPA, and 6FDA because these dianhydrides are readily available and result in polyimides having good properties. Mixtures of dianhydrides are also contemplated and are useful in obtaining the desired solubility in various solvents.

A polyimidesiloxane can be prepared by replacing a portion of the aromatic dianhydride or the diamine with a siloxane-containing dianhydride or a siloxane-containing diamine, respectively. It is preferable not to use both a siloxane diamine and a siloxane dianhydride as it unnecessarily complicates preparation of the polyimide. If a siloxane dianhydride is used, up to 80 mole % of the dianhydride that is present may be siloxane dianhydride, and preferably about 10 to about 50 mole % is siloxane dianhydride. Examples of suitable siloxane dianhydrides can be found in U.S. Pat. No. 4,794,153, herein incorporated by reference, and include siloxane dianhydrides having the formula

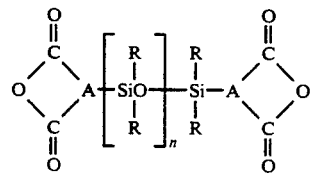

where each A is independently selected from an aromatic group, each R is independently selected from alkyl to $C_8$, alkenyl to $C_8$, and aryl to $C_{10}$, and n is 1 to 50.

About 0 to about 50 mole % of the diamine in the polymer can be a siloxane diamine. If the diamine is the source of siloxane (rather than the dianhydride), then it is preferable to use about 5 to about 30 mole % siloxane diamine. The siloxane diamine has a general formula

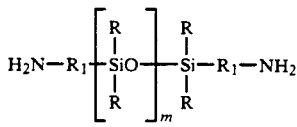

where each $R_1$ is a diradical independently selected from a substituted or unsubstituted aliphatic group having 1 to 12 carbon atoms or a substituted or unsubstituted aromatic group having 6 to 10 carbon atoms, and m is 1 to 200 and is preferably 1 to 20. These diamines are referred to herein by the designation "$G_m$."

About 10 to about 100 mole % of the diamine used to prepare the polyimide, and preferably about 50 to 100 mole %, is an aromatic diamine containing at least one carboxylic acid, but containing no ethylenic unsaturation. Examples of aromatic carboxylic acid diamines include compounds having the formula

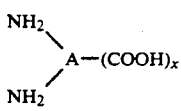

where x is 1, 2, or 3, and is preferably 1. More specifically, examples include compounds having the general formula

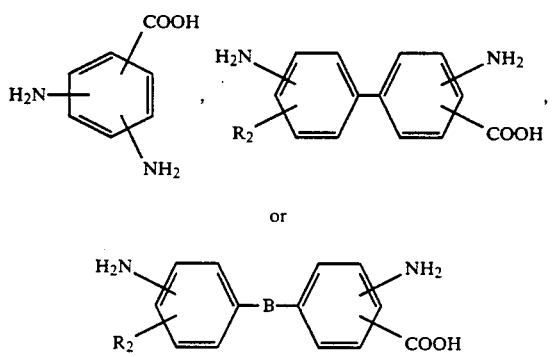

or where $R_2$ is H or COOH, and B is CO, $SO_2$, S, $C(CH_3)_2$, $C(CF_3)_2$, or $CH_2$. The preferred carboxylic acid diamine is 3,5-diaminobenzoic acid because it is commercially available and has been found to work well.

In order to reduce the costs of the polymer and obtain good solubility, it may be desirable to use diamines that are aromatic but do not contain siloxane groups or carboxylic acid groups to prepare the polyimide. While up to 80 mole % of the diamine in the polyimide ca be this third diamine, it is preferable to use no diamine other than the siloxane diamine and the carboxylic acid diamine as this third diamine tends to diminish the desirable properties of the polyimide. Examples of such diamines that can be used include
2,4-diaminotoluene (TDA);
2,5-diaminotoluene;
2,6-diaminotoluene;
m-xylyl diamine;
2,4-diamine-5-chlorotoluene;
2,4-diamine-6-chlorotoluene;
2,2-bis(4[4-aminophenoxyl]phenyl) propane (BAPP);
trifluoromethyl-2-4-diaminobenzene;
m-phenylenediamine;
p-phenylenediamine;
2,2'-bis(4-aminophenyl)-hexafluoropropane (6F diamine);
2,2-bis (4-phenoxy aniline) isopropylidene;
trifluoromethyl-2,4-diaminobenzene;
trifluoromethyl-3,5-diaminobenzene;
2,4,6-trimethyl-1,3-diaminobenzene;
3,4'-oxydianiline;
4,4'-oxydianiline (ODA);
m,m-methylene dianiline;
m,m-sulfone dianiline;
4,4'-diamino-2,2'-trifluoromethyl diphenyloxide;
3,3'-diamino-5,5'-trifluoromethyl diphenyloxide;
4,4'-trifluoromethyl-2,2'-diamino biphenyl;
2,4,6-trimethyl-1,3-diaminobenzene;
o,m-sulfone dianiline; and
diaminoanthraquinone.

The preferred diamines are 6F diamine, BAPP, TDA, and ODA because they are readily available and work well.

Any solvent that will dissolve both the monomers and the polyimide can be used to form a solution of the monomers. Examples of solvents that may be suitable include N-methyl pyrrolidone (NMP), diglyme, triglyme, dimethylformamide, and methyl ethyl ketone. The preferred solvent is NMP because it solubilizes many polyimides. A polyimide can be prepared by forming a solution, preferably about 10 to about 35 wt % solids, of stoichiometric quantities of diamine and dianhydride and heating to about 140 to about 170° C. for about 1 to about 4 hours.

The polyimide ammonium salt is prepared by mixing the polyimide with an ethylenically unsaturated amine. The pendant carboxylic acid groups on the polyimide react stoichiometrically with the amine and it is preferable to use an equivalent amount of amine. The reaction between the carboxylic acid groups and the ethylenically unsaturated amine is immediate and occurs at room temperature. Preferred ethylenically unsaturated amines have the formula

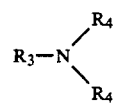

where $R_3$ is an ethylenically unsaturated group, and each $R_4$ is independently selected from $R_3$, hydrocarbon, or hydrogen. Primary, secondary, or tertiary amines can be used, but tertiary amines are preferred as they seem to produce better properties, and tertiary amines having three unsaturated groups are particularly preferred as they introduce more unsaturation into the polymer, resulting in better crosslinking and better resolution. Examples of tertiary amines include
triallylamine;
trimethallylamine;
dimethylallylamine;
N-allyl-N-methylaniline;
4-vinyl pyridine;
dimethylaminoethylacrylate;
dimethylaminoethylmethacrylate;
diethylaminoethylmethacrylate; and
diethylaminoethylacrylate.
Examples of secondary amines include
N-allylaniline;
N-allyl cyclohexylamine; and
diallylamine.
Examples of primary amines include allylamine;
amino ethylmethacrylate;
4-allyl benzylamine; and
amino ethylacrylate.

A preferred polyimide ammonium salt has the repeating units

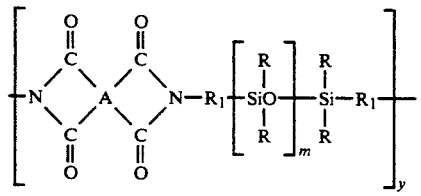

and

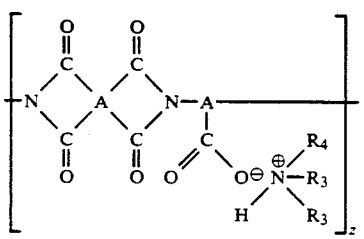

where y is 5 to 30 mole % of y+z.

While the polyimide ammonium salt can be crosslinked without a crosslinking agent, it is preferable to use a crosslinking agent to obtain faster and more complete crosslinking. A composition is preferably prepared of a solution of the polyimide ammonium salt and about 1 to about 30 weight % (based on polymer weight) of a crosslinking agent. Suitable crosslinking agents include trimethylol triacrylate, pentaerythritol triacrylate, pentaerythritol tetraacrylate, pentaerythritol tetramethacrylate, 1,1,1-trimethylolpropane triacrylate, 1,1,1-trimethylolpropane trimethacrylate, 1,1,1-trimethylolpropane trimethacrylate, tetraethylene glycol diacrylate, and tetraethylene glycol dimethacrylate. To incorporate more unsaturated bonds into a crosslinking molecule, the following novel crosslinking agents can be used:

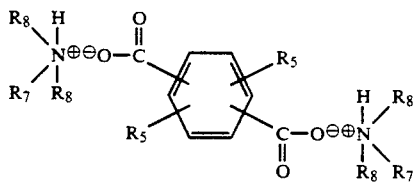

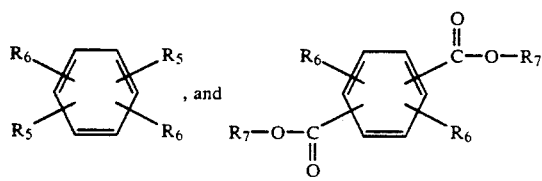

where
$R_5$ is

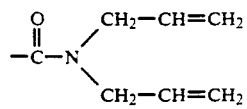

$R_6$ is

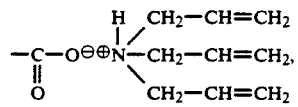

$R_7$ is

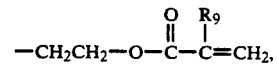

$R_8$ is alkyl to $C_8$, preferably methyl or ethyl, and
$R_9$ is H or $CH_3$.

The preparation of the above three novel crosslinking agents is given in Examples 4, 5, and 6, respectively.

To prepare a coating of the polyimide ammonium salt on a substrate, the composition is spread on the substrate and the solvent is evaporated. Those portions of the coating that one wishes to remain on the substrate are exposed to a actinic radiation (e.g., ultraviolet light), which crosslinks and insolubilizes the coating. The unexposed portions of the coating are washed away with a solvent. While the coatings of this invention are most suitable for use on semiconductor packaging, they can also be used to coat other substrates such as ceramic substrates, polymer films, and metals.

The following examples further illustrate this invention.

EXAMPLE 1

To a 250 ml. 3 neck round bottom flask equipped with overhead stirrer and a Dean Stark trap was added 100 ml N-methyl pyrrolidone, 10 ml toluene, and 14.35 grams oxydiphthalic anhydride. The mixture was stirred and 5.64 grams of 3,5-diaminobenzoic acid was added. After stirring for 30 minutes, 5.01 grams of diaminopropyl terminated dimethyl siloxane oligomer having an average repeat unit of 5 ($G_5$) was added. The mixture was stirred for 1 hour, 0.38 g of 1,4-diazabicyclo[2.2.2.]octane, and 5 ml toluene were added, and the mixture was heated to 170° C. to remove water and toluene. After 90 minutes, the mixture was cooled to room temperature and poured onto water to precipitate the polymer. The slurry was filtered, the polymer reslurried in water, filtered, and dried. The polymer had an inherent viscosity of 0.35 and had 1.62 milliequivalents (meq) of acid per gram (theoretical value=1.59 meq/gram).

EXAMPLE 2

In similar fashion as Example 1, a polymer was obtained using 9.35 pbw (parts by weight) oxydiphthalic anhydride, 3.04 pbw 3,5-diaminobenzoic acid, and 2.48 pbw 1,3-bis(3-amino propyl)-1,1,3,3-tetramethyldisiloxane-($G_1$).

EXAMPLE 3

In similar fashion as Example 1, a polymer without siloxane groups was prepared using 9.3 pbw oxydiphthalic anhydride, and 4.56 pbw 3,5-diaminobenzoic acid.

EXAMPLE 4

A crosslinking agent effective in photosensitive formulations was prepared by completely dissolving 2.2 g of PMDA in 5 ml of NMP and cooling the solution to 5° to 10° C. in an ice bath. To the solution was added dropwise 1.94 g of diallylamine and 3.7 g diethylaminoethyl methacrylate in 5 ml NMP over 30 to 60 minutes. The reaction was run for 4 hours. The solution was used in Examples 8 to 13, 17, and 18.

EXAMPLE 5

A crosslinking agent effective in photosensitive formulations was prepared by cooling 2.2 g of PMDA dissolved in 5 ml of NMP to 5° to 10° C. in an ice bath. During a one hour period, 1.94 g of diallylamine and 2.7 g of triallylamine in 5 ml of NMP were added dropwise. The reaction was run for 4 hours. The solution was used in Example 14.

EXAMPLE 6

A crosslinking agent effective in photosensitive formulations was prepared by dissolving 2.2 g PMDA and 2.6 g of hydroxyethylmethacrylate in 5 ml NMP and cooling the solution in an ice bath. To the solution was added dropwise 2.7 g of triallylamine in 5 ml NMP over a one hour period and the reaction was run for 4 hours. The solution was used in Example 15.

EXAMPLES 7 to 16

The polymer of Example 1 was dissolved in NMP to obtain a 20 wt % solution. To 2.5 g of this solution were added a molar equivalent of unsaturated amine, 0.03 pbw benzophenone, 0.015 pbw Michler's ketone, and an optional crosslinking agent.

EXAMPLE 7

The procedure described for Examples 7–16 was followed using the polymer prepared in Example 2.

EXAMPLE 18

The procedure described for Examples 7–16 was followed using the polymer prepared in Example 3.

The solutions were spun onto silicon wafers at 1500 rpm, soft baked for 2 to 3 minutes on an 80° C. hot plate, exposed to UV light through a mask for 5 minutes, developed in a 2:1 vol:vol NMP:methanol solution, and rinsed with isopropanol. The pattern of the mask was observed.

The following table gives the results of Examples 7 to

| Example | Amine pbw | | Crosslinker Solution pbw | | Results |
|---|---|---|---|---|---|
| 7 | 0.151 | Diethylaminoethyl Methacrylate | — | — | Pattern Obtained |
| 8 | 0.151 | Diethylaminoethyl Methacrylate | 0.08 | Example 4 | Pattern Obtained |
| 9 | 0.086 | Vinyl Pyridine | 0.08 | Example 4 | Pattern Obtained |
| 10 | 0.112 | Triallylamine | 0.08 | Example 4 | Pattern Obtained |
| 11 | 0.046 | Monoallylamine | 0.08 | Example 4 | Pattern Obtained |
| 12 | 0.079 | Diallylamine | 0.08 | Example 4 | Pattern Obtained |

-continued

| Example | Amine pbw | | Crosslinker Solution pbw | | Results |
|---|---|---|---|---|---|
| 13 | 0.128 | Dimethylaminoethyl Methacrylate | 0.08 | Example 4 | Pattern Obtained |
| 14 | 0.151 | Diethylaminoethyl Methacrylate | 0.08 | Example 5 | Pattern Obtained |
| 15 | 0.151 | Diethylaminoethyl Methacrylate | 0.08 | Example 6 | Pattern Obtained |
| 16 | 0.151 | Diethylaminoethyl Methacrylate | 0.04 | Pentaerythritol Tetraacrylate (Solid) | Pattern Obtained |
| 17 | 0.151 | Diethylaminoethyl Methacrylate | 0.08 | Example 4 | Pattern Obtained |
| 18 | 0.151 | Diethylaminoethyl Methacrylate | 0.08 | Example 4 | Pattern Obtained |

We claim:

1. A polyimide ammonium salt comprising the reaction product of
   (A) an aromatic polyimide having pendant carboxylic acid groups, said polyimide comprising the reaction product of diamine and aromatic dianhydride, where said diamine comprises aromatic carboxylic acid diamine having at least one carboxylic acid group; and
   (B) an ethylenically unsaturated amine.

2. A polyimide ammonium salt according to claim 1 wherein said aromatic dianhydride is selected from the group consisting of oxydiphthalic anhydride, pyromellitic dianhydride, 2,2'-bis (3,4-dicarboxyphenyl) hexafluoropropane dianhydride, 3,3',4,4'-benzophenone tetracarboxylic dianhydride, 3,3',4,4'-biphenyl tetracarboxylic dianhydride, and mixtures thereof.

3. A polyimide ammonium salt according to claim 1 wherein about 10 to 50 mole % of said aromatic dianhydride is an aromatic dianhydride that contains siloxane.

4. A polyimide ammonium salt according to claim 1 wherein about 5 to about 30 mole % of said diamine is a diamine that contains siloxane.

5. A polyimide ammonium salt according to claim 1 wherein said ethylenically unsaturated amine is a tertiary amine.

6. A polyimide ammonium salt according to claim 5 wherein said tertiary amine has three ethylenically unsaturated groups.

7. A polyimide ammonium salt according to claim 6 wherein said tertiary amine is triallylamine.

8. A polyimide ammonium salt according to claim 1 wherein about 10 to about 100 mole % of said diamine is said aromatic carboxylic acid diamine.

9. A polyimide ammonium salt according to claim 1 wherein said aromatic carboxylic acid diamine has the formula

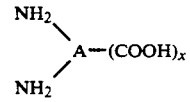

where x is 1, 2, or 3.

10. A polyimide ammonium salt according to claim 9 wherein x is 1.

11. A polyimide ammonium salt according to claim 10 wherein said aromatic carboxylic acid diamine has the formula

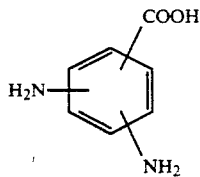

12. A polyimide ammonium salt according to claim 11 wherein said aromatic carboxylic acid diamine is 3,5-diaminobenzoic acid.

13. A polyimide ammonium salt according to claim 9 wherein said aromatic carboxylic acid diamine has the formula

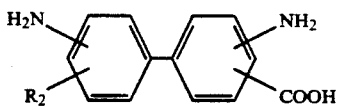

where $R_2$ is H or COOH.

14. A polyimide ammonium salt according to claim 9 wherein said aromatic carboxylic acid diamine has the formula

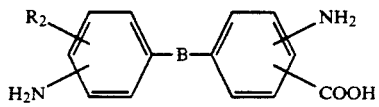

where $R_2$ is H or COOH and B is CO, $SO_2$, S, $C(CH_3)_2$, $C(CF_3)_2$, or $CH_2$.

15. A polyimide ammonium salt according to claim 1 wherein said diamine includes up to 80 mole % of an aromatic diamine that does not contain siloxane and does not have a carboxylic acid group.

16. A polyimide ammonium salt having the repeating units

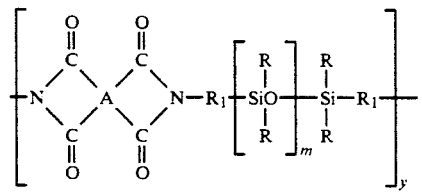

and

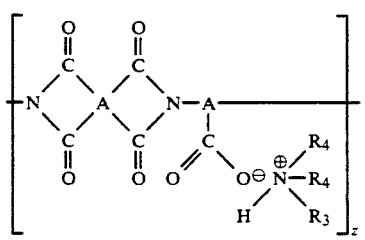

where each A is independently selected from an aromatic group, each R is independently selected from alkyl to $C_8$, alkenyl to $C_8$, and aryl to $C_{10}$, each $R_1$ is a diradical independently selected from a substituted or unsubstituted aliphatic group having 1 to 12 carbon atoms or a substituted or unsubstituted aromatic group having 6 to 10 carbon atoms, $R_3$ is an ethylenically unsaturated group, $R_4$ is $R_3$, hydrocarbon, or hydrogen, m is 1 to 200, and y is 5 to 30 mole % of y+z.

17. A polyimide ammonium salt according to claim 16 wherein $R_1$ is $(CH_2)_3$, R is $CH_3$, and m is 1 to 20.

18. A method of making a polyimide ammonium salt comprising (A) preparing a polyimide having pendant carboxylic acid groups by reacting aromatic dianhydride with diamine, where said diamine comprises a carboxylic acid diamine having at least one carboxylic acid group;

(B) reacting said pendant carboxylic acid groups with an ethylenically unsaturated amine.

19. A method according to claim 18 wherein said polyimide ammonium salt contains the repeating units

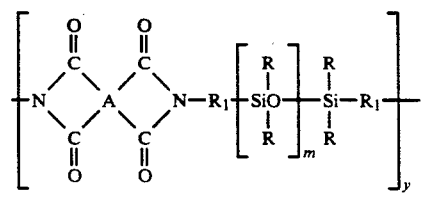

and

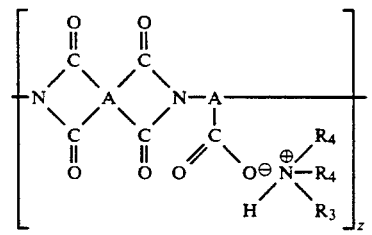

where A is independently selected from an aromatic group, and each R is independently selected from alkyl to $C_8$, alkenyl to $C_8$, and aryl to $C_{10}$, $R_1$ is a diradical independently selected from a substituted or unsubstituted aliphatic group having 1 to 12 carbon atoms or a substituted or unsubstituted aromatic group having 6 to 10 atoms, $R_3$ is an ethylenically unsaturated group, $R_4$ is $R_3$, hydrocarbon, or hydrogen, m is 0 to 200, and y is 5 to 30 mole % of y+z.

20. A composition comprising a solution of polyimide ammonium salt according to claim 1 in an organic solvent and about 1 to about 30 wt % of a crosslinking agent.

21. A composition according to claim 20 wherein said crosslinking agent is selected from the group consisting of

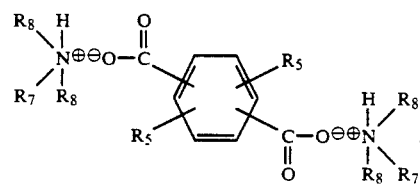

-continued
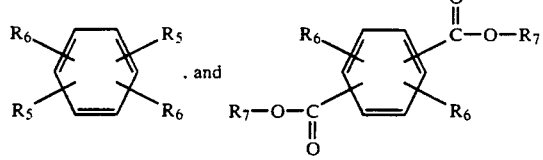
where
R$_5$ is
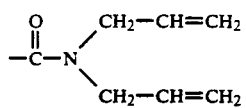
R$_6$ is
R$_7$ is
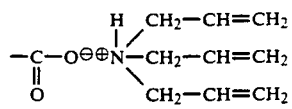
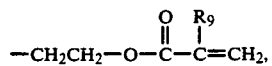
R$_8$ is alkyl to C$_8$, and
R$_9$ is H or CH$_3$.
22. A polyimide ammonium salt according to claim 1 wherein the ethylenically unsaturated group in the ethylenically unsaturated amine portion of said polyimide ammonium salt has been crosslinked.
* * * * *